United States Patent [19]

Althaus et al.

[11] Patent Number: 5,258,504

[45] Date of Patent: Nov. 2, 1993

[54] PROCESS FOR THE PURIFICATION OF STREPTOLYSIN O, INTACT STREPTOLYSIN O OBTAINABLE BY THIS PROCESS

[75] Inventors: Harald Althaus, Wetter; Peter Merle, Marburg, both of Fed. Rep. of Germany

[73] Assignee: Behringwerke Aktiengesellschaft, Marburg, Fed. Rep. of Germany

[21] Appl. No.: 957,811

[22] Filed: Oct. 8, 1992

[30] Foreign Application Priority Data

Oct. 11, 1991 [DE] Fed. Rep. of Germany ....... 4133707

[51] Int. Cl.$^5$ ............................ A23J 3/20; C07K 3/20; C07K 3/28
[52] U.S. Cl. ..................................... 530/417; 530/408; 530/350; 530/412; 435/7.34; 435/885
[58] Field of Search ............... 530/408, 417, 350, 412; 435/7.34, 885

[56] References Cited

U.S. PATENT DOCUMENTS 4,329,151   5/1982   Lou et al. ............................ 436/166

OTHER PUBLICATIONS

Geoffroy et al., "Selective Purification by Thiol-Disulfide Interchange Chromatography . . . ", J. Bio. Chem., vol. 258, No. 16, 1983 pp. 9968-9972.

"Protein Purification Methods," by Harris et al. IRL Press, (1989) pp. 9-11, 57-65.

Alouf et al., Purification & Characterization of "Clostridium perfringens Delta Tokin", Infection and Immunity, vol. 31, No. 2, 1981 pp. 536-546.

Purification of Group C. Streptococcal Extracellular Antigens Detected with Naturally Occurring Human Antibodies: Isolation of Streptokinase and Two Previously Undescribed Antigens, D. Kiefer and S. P. Halbert, Infection and Immunity, 13 (2): 501-512, Feb. 1976.

Nucleotides Sequence of the Streptolysin O (SLO) Gene: Structural Homologies between SLO and Other Membrane-Damaging, Thiol-Activated Toxins Michael A. Kehoe, Lorna Miller, John A. Walker and Graham J. Boulnois Infection and Immunity, 55 (12): 3228-3232, Dec. 1987.

The hydrophobic character of thiol-activated cytolysins, Mary K. Johnson Richard H. Knight, and Gloria K. Drew, Biochem. J., 207: 557-560 (1982).

*Primary Examiner*—Michael G. Wityshyn
*Assistant Examiner*—C. Sayala
*Attorney, Agent, or Firm*—Finnegan, Henderson, Farabow, Garrett & Dunner

[57] ABSTRACT

The invention relates to a process for the purification of streptolysin O (SLO) by means of chromatography and to the use of streptolysin.

13 Claims, No Drawings

PROCESS FOR THE PURIFICATION OF STREPTOLYSIN O, INTACT STREPTOLYSIN O OBTAINABLE BY THIS PROCESS

DESCRIPTION

The invention relates to a process for the purification of streptolysin O (SLO) by means of chromatography and to the use of streptolysin.

Streptolysin O (designated SLO below) is an extracellular, cytolytic toxin which is formed by bacteria of the genus streptococcus. When humans are infected with streptococci, antibodies against SLO are formed, which are of diagnostic significance.

Because of proteolytic activity in the cultures of streptococci, it has hitherto not been possible to isolate relatively large amounts of intact SLO having a molecular weight of 60,000 D. It is predominantly a proteolytically degraded SLO having a molecular weight of about 53,000 D which is isolated. It is also known that SLO can be reversibly inactivated by atmospheric oxygen and activated by thiol compounds. All known processes for the purification of SLO are very laborious, include expensive process steps and give only low yields of highly pure material and are therefore unsuitable for the purification of SLO on a production scale. In Biochem. J. 207, 557-560 (1982) it is described that it did not prove possible to obtain SLO in active form by means of hydrophobic interaction chromatography.

Surprisingly, it has been found that it is possible to bind SLO, for example from a culture solution, in the presence of a water-soluble thiol compound and a sufficiently high concentration of ammonium sulfate to phenyl-®Sepharose or another support suitable for hydrophobic interaction chromatography, in a buffer, and to separate it from other protein components by gradient elution in a decreasing ammonium sulfate gradient.

The invention therefore relates to a process for the purification of streptolysin O (SLO), wherein a SLO-containing solution is brought into contact, in the presence of a water-soluble thiol compound and a salt, with a material suitable for hydrophobic interaction chromatography, in a buffer, and eluted by gradient elution with a solution of a salt using a negative concentration gradient, which starts at a concentration which is lower than the concentration of the salt for the adsorption, and the fraction which contains the SLO is obtained.

Using this simple process it is possible to isolate biologically highly active SLO, which is substantially free from accompanying enzymes, in high yields. In contrast to the SLO products described in the literature, the SLO purified by the present process is not proteolytically fragmented, that is to say is intact SLO.

The SLO-containing solution can be a culture concentrate of streptococci, preferably hemolytic streptococci.

However, the SLO in such a solution can also be a product produced by genetic engineering. Said product can have the natural structure or an allelic structure or can even be a derivative.

The invention therefore also relates to intact streptolysin O obtainable by the process described.

The salt used for the adsorption is preferably ammonium sulfate. However, any other salt which shows a salting-out effect on proteins can be used. In the case of ammonium sulfate, the concentration is between 15% and 25% of the saturation concentration.

The thiol compound is a compound which cleaves protein disulfide bonds, preferably β-mercaptoethanol, thioglycerol, thioglycolate or dithiothreitol.

The buffer used for the chromatography is preferably an alkaline buffer, preferably of pH 7.5-8.5, preferably 0.1M NaHCO$_3$.

The chromatography material preferably contains alkyl or aryl groups on the surface and is preferably phenyl-®Sepharose.

The SLO solution obtained by this process can still be contaminated by proteolytically degraded SLO and by inactive SLO.

Surprisingly, it was found that it is possible to remove the inactive or proteolytically degraded SLO molecules from such a solution, and to obtain highly active intact SLO, by gel permeation chromatography in the presence of a thiol compound, for example on Sephacryl ® S300 HR or another chromatography material having similar separation characteristics.

The thiol compound in the gel chromatography is likewise preferably a compound which cleaves protein disulfide bonds and in particular β-mercaptoethanol, thioglycerol, thioglycolate or dithiothreitol.

Preferably, the chromatography is carried out in a buffer having an alkaline pH, preferably of pH 7.5-8.5, preferably in 0.1M NaHCO$_3$.

The chromatography buffer can additionally contain a salt, preferably sodium chloride, preferably in a concentration of 0.2M-2M.

Following this chromatography step, SLO is in the form of a highly pure and hemolytically highly active preparation, which remains stable over a period of months if stored under sterile and cool conditions.

The amino-terminal amino acid sequence found was NH2-Asp-Ser-Asn-Lys-Gln-Asn-Thr-Ala-Asn-Thr-(SEQ ID NO.:1).

The SLO prepared in this way can be used as test antigen in diagnostic systems which determine the antibodies against SLO in human serum or blood plasma. The specificity of the test systems is better because of the high degree of purity of the SLO used.

Furthermore, the SLO prepared according to the invention is suitable for the isolation, by means of immune affinity chromatography, of highly specific human or animal antibodies against SLO, which antibodies, in turn, can serve as highly specific standards when used in diagnostic test systems.

EXAMPLES

Example 1 a. Preparation of the Starting Material 20 liters of a culture supernatant of Streptococcus pyogenes H46A were prepared in the manner described by Kiefer, D. et al., Infect. Immun. 13(2), 1976, p. 501-512. The culture supernatant clarified by centrifuging was concentrated to a volume of 120 ml using an ultrafiltration unit which was fitted with an ultrafilter having a 30 kD exclusion limit.

b. Hydrophobic interaction chromatography 0.1% by volume of β-mercaptoethanol and then 40 ml of saturated ammonium sulfate solution were added, with stirring, to 120 ml of starting material from example a; any precipitate formed was centrifuged off and discarded. The material was introduced onto a column (2.5×30 cm) of phenyl-Sepharose ®, which was equilibrated with 0.1M NaHCO$_3$, 25% ammonium sulfate and 0.1% by volume β-mercaptoethanol. 400 ml of the equilibration buffer were initially introduced into a gradient mixer. Elution was carried out using a decreasing, linear ammonium sulfate gradient (25% to 0%) in 0.1M NaHCO$_3$, 0.1% by volume β-mercaptoethanol.

The eluate was collected in fractions.

The fractions which displayed the highest hemolytic activity (see Example 2 for determination) were combined and concentrated to a maximum volume of 10 ml of crude streptolysin in an ultrafiltration unit having a 30 kD exclusion limit.

Example 2

Gel Permeation Chromatography

The crude streptolysin from Example 1 was introduced onto a chromatography column (2.5×80 cm) of Sephacryl ® S-300, which was equilibrated with 0.1M NaHCO$_3$, 1M NaCl and 0.1% by volume β-mercaptoethanol.

Elution was carried out with equilibration buffer using a flow rate of 40 cm/h and the eluate was collected in fractions.

The fractions having the highest hemolytic activity were combined and are highly pure SLO.

It was possible to isolate 27 mg of SLO from 20 l of starting material according to a.

Analysis:

A SDS-polyacrylamide electrophoresis of SLO in comparison with the various proteins of known molecular weight (standard no. 4, Serva, gel system according to Lämmli with 10% acrylamide and 0.33% N,N-methylene-bis-acrylamide) was carried out; the protein bands were stained with ®Servablau R250.

The SLO from Example 2 appears as a band having an apparent molecular weight of about 78,000 D.

Amino-Terminal Protein Sequence Analysis of the SLO from Example 2

In a sequence analysis according to Edman it was possible to determine the final 10 amino acids of the amino-terminal end of the protein for the SLO from Example 2. The sequence NH2-Asp-Ser-Asn-Lys-Gln-Asn-Thr-Ala-Asn-Thr-(SEQ ID NO.:1) was found.

In 8 positions the sequence found is in agreement with the amino-terminal sequence of SLO derived from the DNA sequence of Kehoe, M. et al. (Infect.Immun. 55 (12), 1987, p. 3228-3232). Thus, it can be shown that the present product is amino-terminally intact SLO.

Determination of the Hemolytic Activity of SLO

A geometric dilution series of the SLO-containing preparation to be tested in PBS, pH 7.2, which contains 1% (w/v) BSA and 0.1% by volume β-mercaptoethanol, is initially introduced into a 96-well U-shaped microtiter plate (100 μl). 100 μl of a 1% strength (% by volume) freshly prepared rabbit erythrocyte suspension are pipetted into each well of the microtiter plate.

Mixing is carried out by shaking gently.

The plate is incubated for 60 minutes at 37° C. in a humidity chamber. The hemolytic activity is then determined by visual assessment. The reciprocal dilution of the SLO-containing solution which lyses 50% of the erythrocytes in the mixture after the indicated incubation time is given as the titer.

1 HU (hemolytic unit) is the amount of SLO which, under the indicated test conditions, lyses 50% of the erythrocytes employed.

| Fraction | Specific activity (HU/mg) |
| --- | --- |
| Starting material | 12190 |
| SLO, highly pure | 512000 |

Example 3

Purification of Antibodies Against SLO by Means of Immunoaffinity Chromatography 50 mg of a SLO purified according to Example 2 were coupled to cyanogen bromide-activated Sepharose ® 4B (20 ml). The SLO-Sepharose ® was filled into a glass column and equilibrated with PBS, pH 7.2.

The column was loaded with 30 ml of ®Beriglobin (16% strength human immunoglobulin concentrate) diluted with 90 ml of PBS, pH 7.2. Non-bound antibodies were washed out of the column with PBS, pH 7.2. The specific anti-SLO antibody was eluted from the column using 1% by volume acetic acid in distilled water, neutralized immediately with dilute sodium hydroxide solution and concentrated by ultrafiltration. It was possible to isolate 24.6 mg of anti-SLO antibodies from 30 ml of ®Beriglobin.

In an Ouchterlony immunodiffusion of the purified human anti-SLO antibody against SLO starting material according to Example 1, crude SLO according to Example 1 and purified SLO according to Example 2 in comparison with ®Beriglobin, shows precipitate bands against various components of the SLO starting material whereas the purified anti-SLO antibody reacts only with SLO.

We claim:

1. A process for the purification of streptolysin O (SLO), wherein a SLO-containing solution is brought into contact, in the presence of a water-soluble thiol compound and a first salt, with a material suitable for hydrophobic interaction chromatography, in a buffer, and eluted by gradient elution with a solution of a second salt, which can be the same or different as the first salt, using a negative concentration gradient, which starts at a concentration which is lower than the concentration of the first salt for the adsorption, and the fraction which contains the intact SLO is obtained and optionally further purified.

2. The process as claimed in claim 1, wherein the SLO-containing solution is a culture concentrate of streptococci.

3. The process as claimed in claim 1, wherein the SLO-containing solution is a culture concentrate of hemolytic streptococci.

4. The process as claimed in claim 1, wherein the SLO-containing solution is a product prepared by genetic engineering.

5. The process claimed in claim 1, wherein said first salt is any salt suitable for salting out proteins.

6. The process as claimed in claim 1, wherein the thiol compound is a compound which cleaves protein disulfide bonds.

7. The process as claimed in claim 1, wherein the thiol compound is $\beta$-mercaptoethanol, thioglycerol, thioglycolate or dithiothreitol.

8. The process as claimed in claim 1, wherein the buffer is an alkaline buffer.

9. The process as claimed in claim 1, wherein the chromatography material carries alkyl or aryl groups on the surface.

10. The process as claimed in claim 1, wherein the fraction which contains the SLO is further purified by gel permeation chromatography in the presence of a thiol compound.

11. The process as claimed in claim 10, wherein the procedure is carried out in a buffer which contains a salt in a concentration of 0.2M–2M.

12. Substantially pure intact streptolysin O obtainable by the process as claimed in claim 1.

13. The process as claimed in claim 5 wherein said first salt is ammonium sulfate.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Asp  Ser  Asn  Lys  Gln  Asn  Thr  Ala  Asn  Thr
 1              5                         10
```